(12) United States Patent
Hochstetler et al.

(10) Patent No.: US 8,853,438 B2
(45) Date of Patent: Oct. 7, 2014

(54) FORMULATIONS OF SOLUTIONS AND PROCESSES FOR FORMING A SUBSTRATE INCLUDING AN ARSENIC DOPANT

(71) Applicant: Dynaloy, LLC, Kingsport, TN (US)

(72) Inventors: Spencer Erich Hochstetler, Kingsport, TN (US); Kimberly Dona Pollard, Anderson, IN (US); Leslie Shane Moody, Johnson City, TN (US); Peter Borden Mackenzie, Kingsport, TN (US); Junjia Liu, Kingsport, TN (US)

(73) Assignee: Dynaloy, LLC, Kingsport, TN (US)

( * ) Notice: Subject to any disclaimer, the term of this patent is extended or adjusted under 35 U.S.C. 154(b) by 190 days.

(21) Appl. No.: 13/669,087

(22) Filed: Nov. 5, 2012

(65) Prior Publication Data

US 2014/0124896 A1    May 8, 2014

(51) Int. Cl.
*C07F 9/66* (2006.01)
*H01L 21/22* (2006.01)
*H01B 1/00* (2006.01)

(52) U.S. Cl.
USPC ............... 556/72; 556/76; 438/542; 257/607; 252/500

(58) Field of Classification Search
USPC ........ 556/72, 76; 438/542; 257/607; 252/500
See application file for complete search history.

(56) References Cited

U.S. PATENT DOCUMENTS

| | | | |
|---|---|---|---|
| 4,490,192 A | 12/1984 | Gupta et al. | |
| 5,665,845 A | 9/1997 | Allman | |
| 6,323,137 B1 | 11/2001 | Ku et al. | |
| 6,695,903 B1 | 2/2004 | Kübelbeck et al. | |
| 7,064,087 B1 | 6/2006 | Turner et al. | |
| 8,097,305 B2 | 1/2012 | Meyer et al. | |
| 8,466,035 B2 | 6/2013 | Pollard et al. | |
| 8,748,301 B2 | 6/2014 | Morita et al. | |
| 2003/0194636 A1 | 10/2003 | Wanat et al. | |
| 2006/0099831 A1 | 5/2006 | Borovik et al. | |
| 2008/0122005 A1 | 5/2008 | Horsky et al. | |
| 2009/0286349 A1 | 11/2009 | Rohatgi et al. | |
| 2010/0041749 A1* | 2/2010 | Hogg et al. ............ | 514/504 |
| 2011/0081742 A1 | 4/2011 | Barr et al. | |
| 2011/0124187 A1 | 5/2011 | Afzali-Ardakani et al. | |
| 2011/0186969 A1 | 8/2011 | Afzali-Ardakani et al. | |
| 2012/0003826 A1 | 1/2012 | Pollard et al. | |
| 2012/0160306 A1 | 6/2012 | Hirai et al. | |

FOREIGN PATENT DOCUMENTS

| | | |
|---|---|---|
| JP | 2005 123431 A | 5/2005 |
| WO | WO 01/14250 A2 | 3/2001 |
| WO | WO 2011/112546 A1 | 9/2011 |

OTHER PUBLICATIONS

Becker et al., J. Electrochem. Soc.:Solid-State Science and Technology, vol. 134, No. 11, pp. 2923-2931 (1987).*

Ho, Johnny C., et al.; "Controlled Nanoscale Doping of Semiconductors via Molecular Monolayers"; Nature Materials, vol. 7, Issue 1, pp. 62-67 (2008); published online Nov. 11, 2007.
Ho, Johnny C., et al.; "Controlled Nanoscale Doping of Semiconductors via Molecular Monolayers"; Supporting Information; Nature Materials, vol. 7, issue 1, (2007), 10 pages.
Ho, Johnny C., et al.; "Wafer-Scale, Sub-5 nm Junction Formation by Monolayer Doping and Conventional Spike Annealing"; Nano Letters 9 (2), pp. 725-730, (2009); published online Jan. 22, 2009.
Sieval, Alexander B., et al.; An Improved Method for the Preparation of Organic Monolayers of 1-Alkenes on Hydrogen-Terminated Silicon Surfaces; Langmuir 1999, vol. 15, pp. 8288-8291.
Leftwich, Timothy R., et al.; "Chemical manipulation of multifunctional hydrocarbons on silicon surfaces", Surface Science Reports 63, (2008), pp. 1-71.
Tapia-Benavides, Antonio R., et al.; "Do Spiroarsoranes Exhibit Polytopal Equilibrium in Solution?", Inorg. Chem. 2010, 49, pp. 1496-1502.
Dale, Arild J., et al.; "The Preparation and Dynamic Stereochemistry of Oxyarsoranes Containing Five- and Six-membered Ring Systems", Acta Chemica Scandinavica B 29, (1975), pp. 741-748.
Loiseau, P.M., et al.; "Design, Synthesis and Biological Study of New Antiparasitic Spiroarsoranes"; Arzneim.-Forsch./ Drug Res. 43 (II), Nr. 9, (1993), pp. 1004-1009.
Betz, Richard, et al.; "From Simple Diols to Carbohydrate Derivatives of Phenylarsonic Acid"; Inorganic Chemistry 2009, 48, pp. 925-935.
International Search Report with an International filing date Mar. 8, 2011, International Application No. PCT/US 11/27493.
Co-pending U.S. Appl. No. 13/645,239 with a filing date of Oct. 5, 2012.
USPTO Notice of Allowance dated Feb. 14, 2012 in co-pending U.S. Appl. No. 13/042,541.
Co-pending U.S. Appl. No. 13/875,566, filed May 2, 2013, Kimberly Dona Pollard et al. (published as 2013-0260545).
USPTO Office Action dated Jul. 8, 2013 in co-pending U.S. Appl. No. 13/042,541.
USPTO Office Action dated Sep. 13, 2013 in co-pending U.S. Appl. No. 13/875,566.
USPTO Notice of Allowance dated Mar. 27, 2014 in co-pending U.S. Appl. No. 13/042,541.
International Search Report and Written Opinion with date of mailing Apr. 24, 2014 for International Application No. PCT/US2013/068426.
Co-pending U.S. Appl. No. 14/272,482, filed May 7, 2014, Monika Karin Wiedmann et al.

(Continued)

*Primary Examiner* — Porfirio Nazario Gonzalez
(74) *Attorney, Agent, or Firm* — Dennis V. Carmen

(57) ABSTRACT

Formulations of solutions and processes are described to form a substrate including a dopant. In particular implementations, the dopant may include arsenic (As). In an embodiment, a dopant solution is provided that includes a solvent and a dopant. In a particular embodiment, the dopant solution may have a flashpoint that is at least approximately equal to a minimum temperature capable of causing atoms at a surface of the substrate to attach to an arsenic-containing compound of the dopant solution. In one embodiment, a number of silicon atoms at a surface of the substrate are covalently bonded to the arsenic-containing compound.

34 Claims, 4 Drawing Sheets

(56) References Cited

OTHER PUBLICATIONS

Ho, Johnny C., et al.; "Nanoscale doping of InAs via sulfur monolayers"; Applied Physics Letters, 95, 072108 (2009).

Sieval, A.B., et al.; "Highly Stable Si-C Linked Functionalized Monolayers on the Silicon (100) Surface"; Langmuir, 1998, 14, 1759-1768.

Scheres, Luc, et al.; "Organic Monolayers onto Oxide-Free Silicon and Improved Surface Coverage: Alkynes versus Alkenes"; Langmuir, 2010, 26(7), 4790-4795.

Boukherroub, Rabah, et al.; Insights into the Formation Mechanisms of Si-OR Monolayers from the Thermal Reactions of Alcohols and Aldehydes with Si(111)-H[1]; Langmuir, 2000, 16, 7429-7434.

Sauer, D.E., et al.; "Ultrahigh vacuum surface analysis of silicon (100) treated in aqueous hydrofluoric acid and buffered hydrofluoric acid solutions"; Applied Surface Science, 78, (1994), 47-55.

Lafranzo, Natalie A., et al.; "Arsonic Acid Self-Assembled Monolayers Protect Oxide Surfaces from Micronewton Nanomechanical Forces"; Adv. Funct. Mater., 2013, 23, 2415-2421.

Becker, Frank S., et al.; "Low Pressure Deposition of Doped $SiO_2$ by Pyrolysis of Tetraethylorthosilicate (TEOS) II. Arsenic Doped Film"; J. Electrochem. Soc., vol. 136, No. 10, Oct. 1989, 3033-3043.

Baer, Carl D., et al.; "Kinetics of the Hydrolysis of Arsenate(V) Triesters"; Inorg. Chem., 1981, 20, 905-907.

Kuhn, B., et al.; "Versuche zur quantitativen Bestimmung des Arsens nach dem Marsh'schen Verfahreh. Verhalten des Arsenwasserstoffes zu Aktzkali"; Berichte der Deutchen Chemischen Gesellschaft, 23, 1798-1803.

Musil, Stanislav, et al.; "Speciation without Chromatography using Selective Hydride Generation: Inorganic Arsenic in Rice and Samples of Marine Origin"; Analytical Chemistry, 2014, 86, 993-999.

Longo, Robert C., et al.; "Monolayer Doping via Phosphonic Acid Grafting on Silicon: Microscopic Insight from Infrared Spectroscopy and Density Functional Theory Calculations"; Adv. Funct. Mater., 2013, 23, 3471-3477.

Thissen, Peter, et al.; "Activation of Surface Hydroxyl Groups by Modification of H-Terminated Si(111) Surfaces"; J. Am. Chem. Soc., 2012, 134, 8869-8874.

USPTO Notice of Allowance dated Jul. 8, 2014 in co-pending U.S. Appl. No. 13/042,541.

Voorthuijzen, W. Pim, et al.; "Local Doping of Silicon Using Nanoimprint Lithography and Molecular Monolayers"; Advanced Materials, 2011, 23, 1346-1350.

* cited by examiner

FORMULATIONS OF SOLUTIONS AND PROCESSES FOR FORMING A SUBSTRATE INCLUDING AN ARSENIC DOPANT

BACKGROUND

Electronic devices typically include one or more components that are formed from semiconductor wafers. The semiconductor wafers include a number of transistors, sometimes on the order of thousands of transistors up to billions of transistors, to accomplish the functions of the electronic devices. In some cases, electronic device designers often attempt to improve the performance of electronic devices and/or increase the functionality of electronic devices while reducing cost, by adding more transistors to semiconductor wafers.

Semiconductor device manufacturers have responded by continuing to decrease the size of the transistors formed on the semiconductor wafers. However, the extent of the decrease in size of the transistors may be limited due to limitations of processes used to form certain components of the transistor. For example, the decrease in size of the p-type or n-type junctions of a transistor may be limited due to the ability of semiconductor manufacturers to effectively dope semiconductor wafers such that the concentration of the dopant in the semiconductor wafer is uniform and at a shallow enough depth to support a smaller junction size.

In particular, as the need for the depth of junctions of transistors to decrease below the 14 nm mark has increased and as transistors have been formed in three-dimensional shapes (e.g. finFETs), semiconductor manufacturers have encountered problems forming properly doped junctions and source/drain extensions, when using traditional doping methods, such as ion implantation. For example, ion implantation of dopants can damage the surface of the substrates, which affects the performance of the junction. Ion implantation may also suffer from limited lateral diffusion control resulting in greater short channel effects which decrease transistor performance. Additionally, since ion implantation is a line of sight doping technique, as the features of three-dimensional transistors decreases, the ion implantation devices are unable to access the entire surface of the substrate, which leads to a non-uniform doping of the substrate surface. When the junctions of transistors included in electronic devices are not uniformly doped, the performance of electronic devices including these transistors can decrease due to the inability of the transistors to signal discrete on and off states.

SUMMARY

This summary is provided to introduce simplified concepts of formulations of solutions and processes to form a substrate including a dopant, such as As. Additional details of example formulations of solutions and example processes are further described below in the Detailed Description. This summary is not intended to identify essential features of the claimed subject matter, nor is it intended for use in determining the scope of the claimed subject matter.

In one embodiment, the disclosure is directed to a process including preparing a solution including a dopant and a solvent. In some embodiments, the dopant may include arsenic. The process may also include contacting a substrate with the solution. In a particular embodiment, the solution may have a flashpoint that is at least approximately equal to a minimum temperature capable of causing attachment between atoms at a surface of the substrate and an arsenic-containing compound in the solution within a duration of at least 2 hours.

In another embodiment, a solution may include a solvent and an arsenic-containing compound. In a particular embodiment, the solution has a flashpoint that is at least approximately equal to a minimum temperature capable of causing attachment between atoms of a substrate and an arsenic-containing compound in the solution within a duration of at least 2 hours.

In an additional embodiment, a substrate may include a surface having a plurality of silicon atoms. The substrate may also include an arsenic-containing compound covalently bonded to at least a portion of the plurality of the silicon atoms.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

This disclosure describes formulations of solutions and processes to form a substrate including a dopant. In particular implementations, the dopant may include arsenic (As). Substrates doped with arsenic may have improved electrical characteristics versus the electrical characteristics of phosphorous doped substrates. For example, the diffusion coefficient for As is significantly lower than the diffusion coefficient for other dopants, such as P. Thus, using As as a dopant may produce doped substrates with junctions that are shallower than doped substrates that include other n-type dopants. Additionally, using As as a dopant may produce a doped substrate that is able to withstand higher temperatures before diffusion of the dopant atoms occurs than substrates that include other n-type dopants. Accordingly, arsenic doped substrates can have improved performance with respect to substrates doped with phosphorous. In some cases, arsenic doped substrates can be used to produce semiconductor wafers that may be used in high performance electronic devices. Furthermore, this disclosure describes formulations and processes that may be used to form a uniformly doped substrate that may include three-dimensional transistor structures with junctions having depths less than 20 nm. In some cases, the substrates formed according to embodiments herein may include silicon-on-insulator substrates, germanium-on-insulator substrates, conventional silicon substrates, silicon substrates that may present multiple crystal orientations (e.g., substrates having a triangular shaped fin where the orientation of Si atoms may be a function of the position of the Si atoms on the three dimensional structure), conventional germanium substrates, or a combination thereof.

Figure 1:
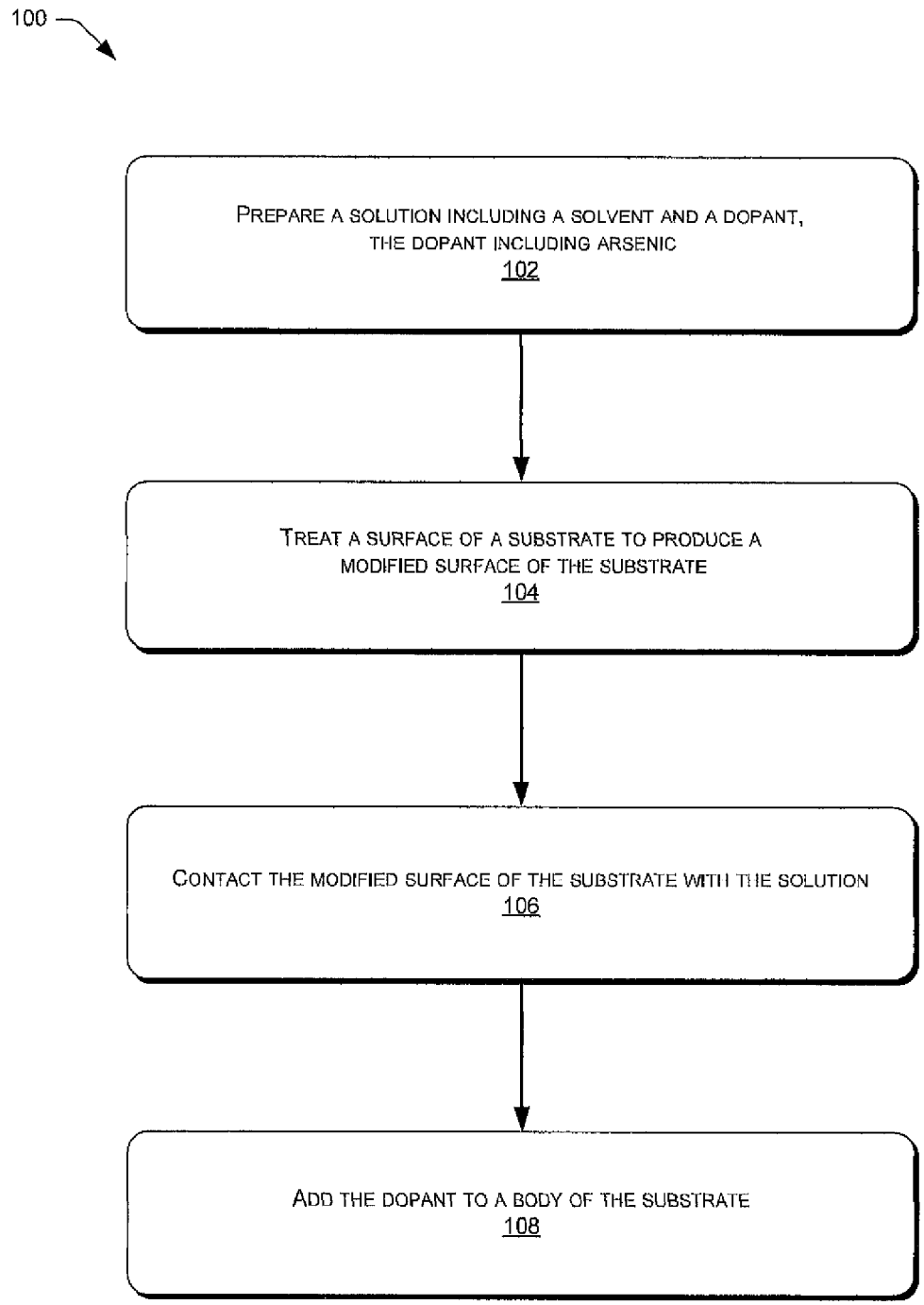
FIG. 1 is a flow diagram of an embodiment of process to form a substrate including a dopant.

FIG. 1 is a flow diagram of a process 100 to form a substrate including an arsenic-containing dopant. In an embodiment, the substrate may be rigid, while in another embodiment, the substrate may be flexible. Additionally, the substrate may include a semiconducting material. For example, in one embodiment, the substrate may be a silicon containing substrate. In another embodiment, the substrate may be a germanium-containing substrate. In still another embodiment, the substrate may include a combination of silicon and germanium. In some cases, the substrate may include at least 40% silicon, at least 55% silicon, or at least 70% silicon. In other cases, substantially all of the substrate may include silicon, no greater than about 95% of the substrate may include silicon, or no greater than about 80% of the substrate may include silicon. In one non-limiting illustrative example, Si atoms of the substrate may have a 100 orientation. In another non-limiting illustrative example, Si atoms of the substrate may have a 111 orientation. In yet another non-limiting illustrative example, Si atoms of the substrate may have a 110 orientation.

At 102, the process 100 includes preparing a solution that includes a solvent and a dopant. In some instances, the solution that includes the solvent and the dopant may be referred to herein as a "dopant solution." In an embodiment, the dopant may include at least one arsenic atom. In one example, the dopant may include an arsenic-containing compound. The arsenic-containing compound may include an inorganic arsenic-containing compound, an organoarsenic compound, or an organic arsenic-containing compound.

In some cases, the arsenic-containing compound may include at least one functional group that is capable of reacting with atoms at the surface of a substrate and/or is capable of interacting with atoms at the surface of the substrate. The at least one functional group of the arsenic-containing compound may react and/or interact with atoms at the surface of the substrate via chemisorption, physisorption, or both. In particular embodiments, the reaction and/or interaction between the at least one functional group of the arsenic-containing compound and atoms at the surface of the substrate may include covalent bonding, dative bonding, hydrogen bonding, ionic bonding, or a combination thereof. In some situations, the arsenic-containing compounds and the atoms at the surface of the substrate may have a localized or supramolecular interaction that is sufficiently strong such that the arsenic-containing compound remains at the surface of the substrate when subjected to some subsequent processing conditions. In other instances, the reaction and/or interaction between the arsenic-containing compound and the atoms at the surface of the substrate may be disrupted when subjected to other subsequent processing conditions, such as the conditions of an annealing process. In this way, the arsenic atoms may be released and available to diffuse into the substrate.

In an illustrative embodiment, the reactive functional group or groups may include an alkenyl group, an alkynyl group, a hydroxyl group, an aryl group, an amine group, an amide group, a nitro group, a carbonyl group, a halogen-containing group, a thiol group, a dienophile, or a combination thereof. Additionally, in some embodiments, the arsenic-containing compounds may include one or more As(III) atoms. In other embodiments, the arsenic-containing compounds may include one or more As(V) atoms. In still other embodiments, the arsenic-containing compounds may include one or more As(III) atoms and one or more As(V) atoms. In some cases, the arsenic-containing compound may be a polyarsenic compound.

The arsenic-containing compounds described in embodiments herein may be formed using a number of techniques. In some cases, the arsenic-containing compounds may be formed from a condensation reaction. Illustrative examples of preparative methods that may be used to form arsenic-containing compounds described in embodiments herein are described in Doak, G. O.; Freedman, L. D. *Organometallic compounds of arsenic, antimony, and bismuth* in; Seyferth, Dietmar, Ed. The Chemistry of Organometallic Compounds; Wiley-Interscience: New York, 1970; *Chemistry of Arsenic, Antimony and Bismuth*; Norman, N. C., Ed. Blackie Academic & Professional: London, 1998; and Raiziss, G. W.; Gavron, J. L. *Organic Arsenical Compounds*; American Chemical Society Monograph Series; Chemical Catalog Company: New York, 1923, which are herein incorporated by reference in their entirety. Other illustrative examples of preparative methods of arsenic-containing compounds described herein are described in Loiseau, P. M., Rekik, L., Madaule, Y., Gayral, P., and Wolf, J. G. Arzneim.-Forsch./Drug Res. 43(II), Nr. 9 (1993) 1004-1009; Dale, Arild J., and Froyen, Paul Acta Chemica Scandanavica B 29 (1975) 741-748; Tapia-Benavides, Antonio R.; Mendoza-Huizar, Luis H.; Perez-Garcia, Francisco; Tlahuext, Hugo; Alvarez, Alejandro; and Tlahuextl, Margarita. Inorg. Chem. 2010, 49, 1496-1502; and Betz, Richard and Klufers, Peter. Inorg. Chem. 2009, 48, 925-935, which are incorporated by reference herein in their entirety. In some embodiments, the arsenic-containing compound may include or be formed from arsonic acids, arsinic acids, derivatives of arsonic acids, derivatives of arsinic acids, or combinations thereof. Derivatives of the arsonic acids and/or derivatives of the arsinic acids may include esters, thioesters, amides, ester/amides, thioester/amides, or a combination thereof. In some embodiments, the arsenic-containing compound may include or be formed from arsonous acids; arsinous acids; derivatives of arsonous and/or arsinous acids, such as esters, amides, and/or ester/amides; or combinations thereof. In other embodiments, the arsenic-containing compounds may include or be formed from arsines, including aminoarsines, alkylaminoarsines, dialkylaminoarsines, haloarsines, dialkylhaloarsines, and dihaloalkylarsines. In still other embodiments, the arsenic-containing compounds may include or be formed from arsine oxides, arseno compounds, diarsines, polyarisnes, or combinations thereof. In an embodiment, the arsenic-containing compounds may serve as an intermediate to produce a dopant or pre-dopant by further reaction to introduce a moiety or moieties capable of reaction or interaction with the surface or modified surface of the substrate via chemisorption or physisorption.

In one illustrative embodiment, arsinic acids may be derivatized to form certain adducts as shown below:

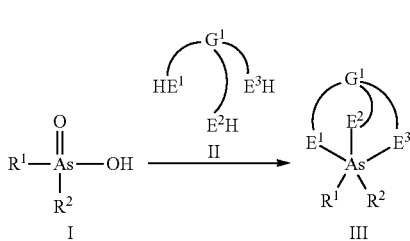

In an embodiment, the composition of $R^1$ and $R^2$ may each, independently, represent a hydrocarbyl group, a substituted hydrocarbyl group, or a silyl group. In addition $R^1$ and $R^2$ may collectively form a bridging group. In another embodiment, $E^1$, $E^2$, and $E^3$, may each, independently, represent N (nitrogen), O (oxygen), or S (sulfur), and if N, then the nitrogen atom, may be further substituted by hydrogen, a hydrocarbyl group, a substituted hydrocarbyl group, or a silyl group. $G^1$ may be a group linking $E^1$, $E^2$, and $E^3$. In addition, $G^1$ may include a hydrocarbyl group, a substituted hydrocarbyl group, or a silyl group.

Non-limiting examples of compound II above may include glycerol, diethanolamine, iminodiacetic acid, 2-ethyl-2-amino-1,3-propanediol, serinol, 2-methyl-2-amino-1,3-propandiol, and trimethylolpropane.

Some non-limiting examples of $R^1$ and $R^2$ may include a methyl group, an ethyl group, a higher branched, straight-chain group, a cycloalkyl group, an alkenyl group, an alkynyl group, an allyl group, a propargyl group, a phenyl group, another aryl group, a hetararyl group, or a combination thereof. For example, $R^1$ and $R^2$ may include 4-hydroxyphenyl, 4-allyloxyphenyl, 4-propargyloxyphenyl, 3-acetamido-4-hydroxyphenyl, 3-amino-4-hydroxyphenyl, 4-aminophenyl, 3-acetamido-4-allyloxyphenyl, 3-acetamido-4-propargyloxyphenyl, 3-nitro-4-hydroxyphenyl, 3-nitro-4-allyloxyphenyl, 3-nitro-4-propargyloxyphenyl, 4-aminophenyl, 4-allylaminophenyl, 4-diallylaminophenyl, 4-propargylaminophenyl, 4-dipropargylaminophenyl, 4-allyloxy-3-allylaminophenyl, 4-allyloxy-3-diallylaminophenyl, 4-propargyloxy-3-dipropargylaminophenyl, 4-maleimidophenyl, 4-hydroxy-3-maleimidophenyl, 4-acrylamidophenyl, 4-methacrylamidophenyl, 4-(2-methoxy-2-oxoethoxy)phenyl, or 4-(4-(methoxycarbonyl)benzamidophenyl)phenyl.

In another illustrative embodiment, arsonic acids, such as compound IV below, may be derivatized to form certain adducts, such as compound VII below, by reaction with compounds V and VI as shown below. In some embodiments, V and VI are the same compound. In other embodiments V and VI are different compounds.

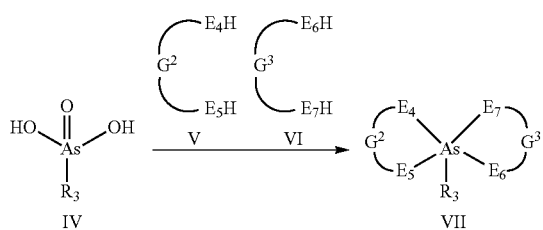

In an embodiment, $R^3$ may include a hydrocarbyl group, a substituted hydrocarbyl group, or a silyl group. Additionally, $E^4$, $E^5$, $E^6$, and $E^7$ may each, independently, represent O, S, or N; and if any of $E^4$, $E^5$, $E^6$, or $E^7$ is N, then the nitrogen atom is further substituted by hydrogen, a hydrocarbyl group, a substituted hydrocarbyl group, or a silyl group. Further, $G^2$ may be a group linking $E^4$ and $E^5$ and $G^3$ may be a group linking $E^6$ and $E^7$. $G^2$ and $G^3$ may collectively form a bridging group and $G^2$ and $G^3$ may include a hydrocarbyl group, a substituted hydrocarbyl group, or a silyl group. In an embodiment, at least one of $R^3$, $G^2$, and $G^3$ includes a moiety or moieties capable of reaction or interaction with the surface or modified surface of the substrate via chemisorption or physisorption and the moiety or moieties borne by at least one of $R^3$, $G^2$, and $G^3$ is selected from the group consisting of: a terminally unsaturated hydrocarbyl; a carboxylate ester; an activated ester; an arsonic acid group; an alkene conjugated to at least one ketone; an alkene conjugated to at least one aldehyde group; an alkene conjugated to at least one cyano group; an alkene conjugated to at least one nitro group; an alkene conjugated to at least one sulfonyl ester; an alkene conjugated to at least one carboxylic ester; an alkene conjugated to at least one activated ester group; and an alkene conjugated to at least one arsonic acid group.

Some non-limiting examples of $R^3$ may include a methyl group, an ethyl group, a higher branched, straight-chain group, a cycloalkyl group, an alkenyl group, an alkynyl group, an allyl group, a propargyl group, a phenyl group, another aryl group, a heteroaryl group, or a combination thereof. In an embodiment, $R^3$ may include 4-hydroxyphenyl, 4-allyloxyphenyl, 4-propargyloxyphenyl, 3-acetamido-4-hydroxyphenyl, 3-amino-4-hydroxyphenyl, 4-aminophenyl, 3-acetamido-4-allyloxyphenyl, 3-acetamido-4-propargyloxyphenyl, 3-nitro-4-hydroxyphenyl, 3-nitro-4-allyloxyphenyl, 3-nitro-4-propargyloxyphenyl, 4-aminophenyl, 4-allylaminophenyl, 4-diallylaminophenyl, 4-propargylaminophenyl, 4-dipropargylaminophenyl, 4-allyloxy-3-allylaminophenyl, 4-allyloxy-3-diallylaminophenyl, 4-propargyloxy-3-dipropargylaminophenyl, 4-maleimidophenyl, 4-hydroxy-3-maleimidophenyl, 4-acrylamidophenyl, 4-methacrylamidophenyl, 4-(2-methoxy-2-oxoethoxy)phenyl, 4-(4-(methoxycarbonyl)benzamidophenyl)phenyl.

Some non-limiting examples of compounds V and VII above are ethylene glycol, propylene glycol, pinacol, mercaptothanol, ethylenediamine, ethanedithol, catechol, 1,2-diaminobenzene, ortho-aminothiophenol, ethanolamine, 2-amino-2-methyl-1-propanol, 2-hydroxyisobutyric acid, 2-aminoisobutyric acid, 2-aminophenol, N-methylethanolamine, 3-allyloxy-1,2-propanediol, 3-amino-4-hydroxyphenylarsonic acid, arsphenamine, 3-amino-4-hydroxyphenylarsonic acid, 2-(tert-butylamino)ethanol, or combinations thereof.

In some embodiments, certain arsines, in particular, di- or trihaloarsines and/or bis- or trisaminoarsines may be further derivatized with bis nucleophiles. For example, bis nucleophiles, such as compound VIII ($HE^9$-$G^4$-$E^8H$), can react with trisdialkylaminoarsines to give a composition of matter of Formula IX:

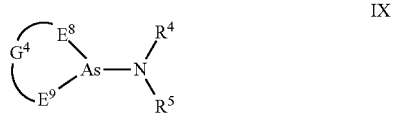

In an embodiment, $R^4$ and $R^5$ may each, independently, include hydrogen, a hydrocarbyl group, a substituted hydrocarbyl group, or a silyl group. In addition, $R^4$ and $R^5$ may collectively form a bridging group. Further, $E^8$ and $E^9$ may each, independently, represent O, S, or N, and if N, then N is further substituted by hydrogen, a hydrocarbyl group, a substituted hydrocarbyl group, or a silyl group. Further, $G^4$ is a group linking $E^8$ and $E^9$ and, $G^4$ may include a hydrocarbyl group, a substituted hydrocarbyl group, or a silyl group. Additionally, $G^4$ may include an alkenyl group or alkynyl group.

Some non-limiting examples of compound VIII may include ethylene glycol, propylene glycol, pinacol, mercaptothanol, ethylenediamine, ethanedithol, catechol, 1,2-diaminobenzene, ortho-aminothiophenol, ethanolamine, 2-amino-2-methyl-1-propanol, 2-hydroxyisobutyric acid, 2-aminoisobutyric acid, 2-aminophenol, N-methylethanolamine, 3-allyloxy-1,2-propanediol, 3-amino-4-hydroxyphenylarsonic acid, arsphenamine, 3-amino-4-hydroxyphenylarsonic acid, 2-(tert-butylamino)ethanol, N,N-bis(hydroxyethyl)-4-propargylyloxyaniline, and N,N-bis(hydroxyethyl)-4-allyloxyaniline.

Table 1 includes illustrative examples of arsenic-containing compounds that may be utilized in embodiments described herein. In addition, the arsenic-containing compounds that may be utilized in embodiments herein may include ions of the compounds listed in Table 1, salts of the compounds listed in Table 1, or a combination thereof.

TABLE 1

| Compound Number | Molecular Weight | Structure |
|---|---|---|
| 1 | 207.15 | 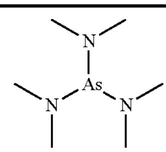 |
| 2 | | 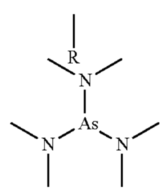 |
| 4 | 138 | 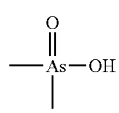 |
| 5 | 202.04 | 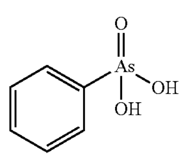 |
| 6 | 166.01 | 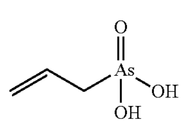 |
| 7 | 384.34 | 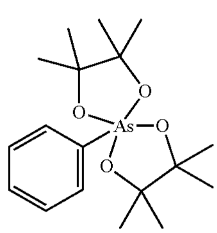 |
| 8 | 326.27 | |
| 9 | 290.23 | |
| 10 | 348.31 | |
| 11 | 235.07 | |
| 12 | 473.31 | |
| 13 | 400.34 | |

TABLE 1-continued

| Compound Number | Molecular Weight | Structure |
|---|---|---|
| 14 | 320.17 | |
| 15 | 472.4 | |
| 16 | 379.2 | |
| 17 | 440.41 | |
| 18 | | |
| 19 | | |
| 20 | | |
| 21 | | 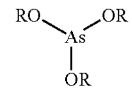 |
| 22 | | 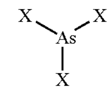 |
| 23 | | 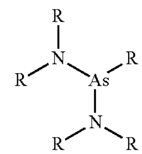 |
| 24 | | 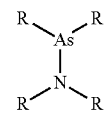 |
| 25 | | 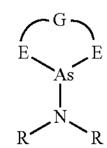 |
| 26 | | 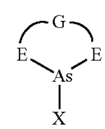 |
| 27 | | 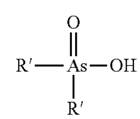 |
| 28 | | 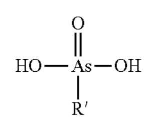 |
| 29 | | 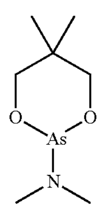 |

In Table 1, each R, may independently, include hydrogen, a hydrocarbyl group, a substituted hydrocarbyl group, or a silyl group. In addition, two or more R groups taken together may collectively form a bridging group. Further, in Table 1, each R' group, may independently, include hydrogen, a hydrocarbyl group, a substituted hydrocarbyl group, or a silyl group. Additionally, two or more R' groups taken together may collectively form a bridging group. E in Table 1 may, independently include N, O, or S atoms. In situations when E is N, then N may be further substituted by hydrogen, a hydrocarbyl group, a substituted hydrocarbyl group, or a silyl group. In Table 1, G may represent a group linking two or more atoms represented by E; and G may include a hydrocarbyl group, a substituted hydrocarbyl group, or a silyl group. Furthermore, in Table 1, X may include a halogen atom.

In an embodiment, a solvent included in the dopant solution may be capable of dissolving the dopant or the dopant may be miscible in the dopant solution at a temperature of no greater than about 50° C., no greater than about 42° C., no greater than about 35° C., no greater than about 30° C., or no greater than about 25° C. In another embodiment, the solvent may be capable of dissolving the dopant at a temperature of at least 2° C., at least 8° C., at least 15° C., or at least about 20° C. In an illustrative embodiment, the solvent may be capable of dissolving the dopant at a temperature within a range of about 20° C. to about 35° C.

In illustrative embodiments, the solvent may include 4-hydroxy butanoic acid, a glycol ether (e.g., di-ethylene glycol di-butyl ether, tetra-ethylene glycol di-methyl ether (tetraglyme)), 4-formylmorpholine, phenylacetic acid, a C9 alcohol, a C10 alcohol, 3-nonanone, phenylpropyl ether, dimethylsulfoxide (DMSO), cyclooctanone, furfuryl acetone, isophorone, di-hexyl ether, 2-nonanone, phenyl propyl ether, hexyl benzene, mesitylene, N-methylpyrrolidone (NMP), an alkanolamine, acetonitrile, toluene, dioxane, tetrahydrofuran (THF), or combinations thereof. In some cases, the solvent may include an inert compound, such as methanol, ethanol, isopropanol, ethylene glycol, propylene glycol, glycerine, ethyl acetate, propyl acetate, methyl acetate, acetone, methyl ethyl ketone, methyl butyl ketone, or combinations thereof.

In particular instances, the solvent may include an amount of water. In some cases, the amount of water included in the solvent may be minimized. For example, the preparation of the solution at 102 may include drying the solvent. To illustrate, the solvent may be dried by adding a drying agent to the solvent. In one embodiment, the drying agent can include an inorganic salt, a zeolite, a water reactive compound, or a combination thereof. In another illustration, the solvent may be dried by washing the solvent with a drying solution. In additional illustrative examples, the solvent may be dried via distillation in the presence of a drying agent in an ambient environment or while pulling a vacuum, via distillation of water from the solvent in an ambient environment or while pulling a vacuum, via rotary evaporation techniques, via thin-film evaporation techniques, via azeotropic distillation techniques, or a combination thereof. In other embodiments, the solvent may be non-hygroscopic.

In one embodiment, the solvent may include no greater than about 10 vol % water for a total volume of the solvent, no greater than about 7 vol % water for a total volume of the solvent, no greater than about 4 vol % water for a total volume of the solvent, or no greater than about 1 vol % water for a total volume of the solvent. In a particular embodiment, the solvent can include within a range of 0.05 vol % water to about 2.5 vol % water for a total volume of the solvent. In an illustrative embodiment, the solvent may be sufficiently dry such that a precipitate is not formed when the dopant and solvent are mixed at suitable process conditions.

In some cases, the dopant solution may have a flashpoint that is at least approximately equal to or greater than a minimum temperature capable of causing attachment between at least a portion of the atoms at a surface of a substrate and an arsenic-containing compound in the dopant solution. In an embodiment, the attachment may occur in conjunction with a reaction between the arsenic-containing compound in the dopant solution and the atoms at the surface of the substrate. In some embodiments, the arsenic-containing compound may attach to at least 5% of the atoms at the surface of the substrate, at least 20% of the atoms at the surface of the substrate, at least 50% of the atoms at the surface of the substrate, at least 80% of the atoms at the surface of the substrate, or at least 95% of the atoms at the surface of the substrate. In a particular embodiment, the arsenic-containing compound may attach to essentially all of the atoms at the surface of the substrate.

In an embodiment, the flashpoint of the dopant solution may be at least 40° C., at least 55° C., at least 75° C., at least 100° C., at least 125° C., at least 150° C., or at least 200° C. In a particular illustrative embodiment, the flashpoint of the dopant solution may be within a range of about 50° C. to about 115° C. In another particular illustrative embodiment, the flashpoint of the dopant solution can be within a range of about 110° C. to about 250° C.

Further, the flashpoint of the dopant solution may be at least 10° C., at least 35° C., at least 50° C., or at least 75° C. greater than the minimum temperature capable of causing attachment between atoms at a surface of the substrate and the arsenic-containing compound of the dopant solution. In another embodiment, the flashpoint of the dopant solution may be no greater than 200° C., no greater than 175° C., no greater than 140° C., or no greater than 100° C. greater than the minimum temperature capable of causing attachment between atoms at a surface of the substrate and the arsenic-containing compound of the dopant solution. In an illustrative embodiment, the flashpoint of the dopant solution may be within a range of about 25° C. to about 150° C. or within a range of about 40° C. to about 80° C. greater than the minimum temperature capable of causing attachment between atoms at a surface of the substrate and the arsenic-containing compound of the dopant solution.

In some situations, the flashpoint of the solution may be at least a temperature that is capable of causing attachment between atoms at the surface of the substrate and the arsenic-containing compound of the dopant solution within a duration of at least 2 hours, at least 2.5 hours, at least 3 hours, at least 5 hours, or at least 7.5 hours. Further, the flashpoint of the solution may be at least a temperature that is capable of causing attachment between atoms at the surface of the substrate and the arsenic-containing compound of the dopant solution within a duration of no greater than 15 hours, no greater than 12 hours, no greater than 10 hours, or no greater than 8 hours. In an embodiment, the flashpoint of the solution may be at least a temperature that is capable of causing attachment between atoms at the surface of the substrate and the arsenic-containing compound of the dopant solution within a duration having a range of about 1.5 hours to about 10 hours. In another embodiment, the flashpoint of the solution may be at least a temperature that is capable of causing attachment between atoms at the surface of the substrate and the arsenic-containing compound of the dopant solution within a duration having a range of about 2.5 hours to about 5 hours. In some scenarios, the flashpoint of the solution may be at least a temperature that is capable of causing attachment between atoms at the surface of the substrate and the arsenic-containing compound of the dopant solution at a pressure within a range of about 5 pounds per square inch (psi) to about 50 psi.

In some embodiments, the solution can include at least 1 wt % dopant of a total weight of the dopant solution, at least 5 wt % dopant of a total weight of the dopant solution, at least 15 wt % dopant of a total weight of the dopant solution, or at least 30 wt % dopant of a total weight of the dopant solution. In other embodiments, the solution includes no greater than about 60 wt % dopant of a total weight of the dopant solution, no greater than about 50 wt % dopant of a total weight of the dopant solution, no greater than about 42 wt % dopant of a total weight of the dopant solution, or no greater than about 35 wt % dopant of a total weight of the dopant solution. In an illustrative embodiment, the solution can include dopant within a range of about 2 wt % to about 11 wt % of a total weight of the dopant solution. In another illustrative embodiment, the solution may include dopant within a range of about 25 wt % to about 40 wt % of a total volume of the dopant solution. In a further illustrative embodiment, substantially all of the dopant solution can include the dopant.

In an embodiment, preparing the dopant solution can include mixing the solvent and the dopant at a suitable temperature and pressure such that the solvent dissolves the dopant or the dopant is miscible in the solvent. For example, the solvent and the dopant can be mixed at a temperature of at least 10° C., at least 18° C., at least 25° C., or at least 30° C. In another example, the solvent and the dopant may be mixed at a temperature of no greater than about 50° C., no greater than about 42° C., or no greater than about 35° C. In an illustrative embodiment, the dopant and the solvent can be mixed at a temperature within a range of about 17° C. to about 30° C. Further, the dopant and the solvent can be mixed at a pressure within a range of about 10 pounds/in.$^2$ (psi) to about 25 psi.

At 104, the process 100 includes treating a surface of the substrate to produce a modified surface of the substrate. In an embodiment, treating the surface of the substrate may include contacting the surface with a material that is capable of modifying the bonds of atoms at the surface of the substrate. "Contacting" as used herein may refer to one or more processes for bringing the surface of the substrate into physical contact with a material, such as immersion, spin coating, spraying, vapor exposure, and the like.

In an embodiment, atoms at the surface of the substrate may oxidize when exposed to air forming an oxide at the surface of the substrate. In some cases, treating the surface of the substrate may include removing at least a portion of the oxide with a particular material. In a particular embodiment, the surface of the substrate can be treated with an acidic solution to replace at least a portion of the oxidized portions of the surface with hydrogen-terminated atoms. In particular embodiments, a first portion of the atoms on the surface of substrate may undergo hydrogen termination, while a second portion of the atoms of the surface of the substrate may remain oxidized. In certain situations, the acidic solution can include a hydrofluoric acid, such as a dilute hydrofluoric acid. In an embodiment, the substrate may be treated with the acidic solution for a duration of at least 1 minute, at least 3 minutes, or at least 5 minutes. In another embodiment, the substrate may be treated with the acidic solution for no greater than 15 minutes, no greater than 12 minutes, or no greater than 8 minutes. In a non-limiting illustrative embodiment, the substrate may be treated with the acidic solution for a duration within a range of about 2 minutes to about 6 minutes. In a further embodiment, the substrate may be treated with the acidic solution at a temperature within a range of about 10° C. to about 35° C. In another embodiment, the substrate may be treated with the acidic solution in an inert environment, such as a $N_2$ environment. In a further embodiment, the substrate may be treated with an acidic solution that has been de-aerated.

In particular embodiments, the surface of the substrate may be treated with other materials to modify the surface of the substrate. In some situations, the substrate may undergo multiple treatments with certain materials to modify the surface of the substrate. Additionally, the surface of the substrate may be modified such that endgroups on the surface of the substrate are reactive toward the arsenic-containing compounds included in the dopant solution prepared with respect to operation 102. In one illustrative example, the surface of the substrate may include a number of silicon atoms that are treated in such a way that silanols are formed followed by contacting the substrate with a solution that includes an ester-containing molecule. In another illustrative example, the surface of the substrate may be contacted with a nitric acid and hydrogen peroxide solution. In some embodiments, the amount of nitric acid in the nitric acid and hydrogen peroxide solution can be within a range of about 10 vol % to about 40 vol % of a total volume of the nitric acid and hydrogen peroxide solution. In other embodiments, the surface of the substrate may be contacted with an aqueous nitric acid solution. In a particular embodiment, an amount of nitric acid in the aqueous nitric acid solution may be within a range of about 10 vol % to about 70 vol % of a total volume of the aqueous nitric acid solution. In further illustrative examples, atoms at the surface of the substrate may be treated to form hydrides followed by contacting the substrate with a solution that can include an allyl-containing molecule. To illustrate, silicon atoms at the surface of the substrate may be treated to form silicon hydrides and then undergo hydrosilylation by contacting the surface of the substrate with an allyl-containing solution to form a silicon-alkyl bond. Other illustrative examples of the chemical modification of the surface of a substrate that may be used in embodiments herein are described in, Timothy R. Leftwich, Andrew V. Teplyakov. "Chemical Manipulation of Multifunctional Hydrocarbons on Silicon Surfaces." Surface Science Reports 63 (2008): 1-71, which is incorporated by reference herein in its entirety.

In an illustrative embodiment, the surface of the substrate may be modified by contacting the surface with a solution for a duration of at least 2 minutes, at least 5 minutes, at least 20 minutes, or at least 45 minutes. In another illustrative embodiment, the surface of the substrate may be modified by contacting the surface with a solution for a duration of no greater than about 125 minutes, no greater than about 100 minutes, or no greater than about 75 minutes. In a non-limiting illustrative embodiment, the surface of the substrate may be modified by contacting the surface with a solution for a duration within a range of about 40 minutes to about 80 minutes.

Further, the surface of the substrate may be modified by contacting the surface with a solution at a temperature of at least 25° C., at least 55° C., or at least 80° C. In other situations, the substrate may be modified by contacting the surface with a solution at a temperature of no greater than about 150° C., no greater than about 120° C., or no greater than about 95° C. In a non-limiting illustrative embodiment, the surface of the substrate may be modified by contacting the surface at a temperature within a range of about 65° C. to about 100° C.

In some instances, treating the surface of the substrate to produce a modified surface of the substrate may include one or more rinse cycles, one or more drying cycles, or a combination thereof. In one example, after hydrosilylation of the surface of the substrate, the substrate may be rinsed with a solution including a solvent. In one embodiment, the solvent can include isopropyl alcohol. In another embodiment, the solvent can include mesitylene. In a further embodiment, the solvent can include DMSO. In another example, after modification of the surface of the substrate, the substrate may be rinsed with de-ionized water. Additionally, the substrate may be rinsed after contacting the surface of the substrate with a surface modification solution. In other embodiments, after a rinsing cycle, the substrate may be dried. The substrate may be dried via air drying, Marangoni drying, spin drying, contacting the substrate with a stream of dry inert gas, or a combination thereof.

At 106, the process 100 may include contacting the modified surface of the substrate with the dopant solution prepared with respect to operation 102. Contacting the modified surface of the substrate with the dopant solution may cause a reaction between atoms of the modified surface of the substrate and the arsenic-containing molecules in the dopant solution. In this way, arsenic-containing compounds can be chemisorbed or physisorbed to atoms at the surface of the substrate. In particular, the arsenic-containing compounds may have a localized or supramolecular interaction that is sufficiently strong such that the arsenic-containing compound remains on the surface of the substrate when subjected to subsequent processing. In some cases, the interaction between the arsenic-containing compound and the atoms at the surface of the substrate may include covalent bonding, dative bonding, hydrogen bonding, ionic bonding, or a combination thereof. Particular examples of interactions between arsenic-containing compounds and atoms on the surface of the substrate may include hydrosilylation of alkenes and/or alkynes with surface silanes; ester interchange between ester moieties and surface silanols of other attached hydroxyls; carboxamide formation from an ester and amino functionalized surface; arsonous and/or asinous ester formation from surface silanols and amino arsines, such as trisdimethylaminoarsine; arsonous or arsinous ester formation from surface silanols and arsenic(III)-containing compounds, such as for example, arsenic-amine compounds with no more than 1 arsenic-nitrogen bond, no more than 2 arsenic-nitrogen bonds, or no more than 3 arsenic-nitrogen bonds; or combinations thereof.

In one embodiment, the surface of the substrate can be contacted with the dopant solution for a duration of at least 0.05 hours, 0.3 hours, at least 0.9 hours, at least 1.4 hours, or at least 1.8 hours. In another embodiment, the surface of the substrate can be contacted with the dopant solution for a duration of no greater than about 3.6 hours, no greater than about 3.1 hours, no greater than about 2.5 hours, or no greater than about 2.2 hours. In one illustrative embodiment, the surface of the substrate can be contacted with the dopant solution for a duration within a range of about 0.4 hours to about 3.0 hours. In another illustrative embodiment, the surface of the substrate can be contacted with the dopant solution for a duration within a range of about 0.7 hours to about 2 hours.

In another embodiment, the surface of the substrate may be contacted with the dopant solution at a temperature of at least 30° C., at least 55° C., at least 80° C., or at least 105° C. In other embodiments, the surface of the substrate may be contacted with the dopant solution at a temperature of no greater than about 175° C., no greater than about 155° C., no greater than about 135° C., or no greater than about 120° C. In an illustrative embodiment, the surface of the substrate can be contacted with the dopant solution at a temperature within a range of about 85° C. to about 140° C. or within a range of about 100° C. to about 125° C.

In some scenarios, the substrate may be rinsed after being contacted by the dopant solution. In one embodiment, the substrate may be rinsed with the solvent included in the dopant solution. In one illustrative example, the substrate may be rinsed with tetraglyme when tetraglyme is used to prepare the solution of 102. In another illustrative example, the substrate can be rinsed with acetonitrile when acetonitrile is used to prepare the solution of 102. In an additional illustrative example, the substrate can be rinsed with THF when THF is used to prepare the solution of 102. In an additional illustrative example, the substrate can be rinsed with n-methylpyrolidone (NMP) when NMP is used to prepare the solution of 102. In certain instances, the substrate may undergo an additional rinse after being rinsed with the solvent included in the dopant solution. In a non-limiting illustrative embodiment, the substrate may undergo an additional rinse using a low boiling point solvent. An example of a low boiling solvent may be isopropanol. In yet another illustrative example, the substrate can be rinsed with water. In certain cases, the substrate may also undergo one or more drying operations. In one case, the substrate may be dried after being contacted with the dopant solution. In another case, the substrate may be dried after being rinsed with the solvent of the dopant solution. In a further scenario, rinsing the substrate with the low-boiling point solvent may be part of a process to dry the substrate. In some cases, the substrate may not undergo rinsing after modifying the surface of the substrate and before contacting the substrate with a dopant solution.

In an embodiment, rinsing can include contacting the substrate with a heated solvent, such as the solvent included in the dopant solution. In a particular embodiment, the temperature of the solvent may be room temperatures, such as within a range of about 15° C. to about 25° C., up to a minimum temperature capable of initiating a reaction between the dopant solution and the substrate within a specified duration. In some cases, the heated solvent may be applied to a substrate after contacting the surface of the substrate with a surface modification solution or after the substrate has been contacted with a dopant solution. In one embodiment, after contacting the substrate with the heated solvent, the substrate may be rinsed with either water or a low boiling organic solvent.

In another situation, rinsing the substrate can include contacting the substrate with a solvent and providing sonic energy into the liquid. In some instances, the sonic energy may be ultrasonic or megasonic. In one embodiment, the sonic energy may be provided to the solvent for a duration of at least 10 seconds, at least 30 seconds, at least 2 minutes or at least 5 minutes. In a particular embodiment, the sonic energy may be provided continuously or in a pulsed manner, and the frequency may be fixed, swept, or any combination thereof. In a further embodiment, the solvent provided with the sonic energy may be the solvent present in the dopant solution, another organic solvent, such as a low boiling organic solvent, or de-ionized water.

In a particular illustrative embodiment, the processes described with respect to operation 106 can be repeated. To illustrate, after the substrate is contacted with the dopant solution, the substrate may undergo an additional process to contact the substrate with the dopant solution. In some situations, the substrate may be rinsed each time the substrate is contacted with a dopant solution, while in other cases, the substrate may not be rinsed after at least one of the applications of the dopant solution to the substrate. Accordingly, multiple layers of the arsenic-containing compound in the dopant solution may be added to the surface of the substrate. In some instances, the duration and temperature of subsequent operations of contacting the substrate with the dopant solution may be similar to the duration and temperature of a previous operation of contacting the substrate and the dopant solution. In other instances, the duration and temperature of subsequent operations directed to contacting the substrate with the dopant solution may be different than the duration and temperature of a previous operation of contacting the substrate with the dopant solution. Accordingly, the use of more than one dopant solution for the corresponding dopant layers may be employed.

At 108, the process 100 includes adding the dopant to a body of the substrate. In some cases, the dopant may be added to the body of the substrate via diffusion. In particular instances, arsenic atoms included in the arsenic-containing compounds bonded to the surface of the substrate may diffuse from the surface of the substrate into the body of the substrate under suitable conditions. In some cases, the arsenic-containing compounds bonded to the surface of the substrate may be organoarsenic compounds. In other situations, the arsenic-containing compounds bonded to the surface of the substrate may be inorganic. In a particular instance, organic functional groups of an organoarsenic compound that is bonded to atoms at the surface of the substrate may react with trace amounts of water to cleave the organic functional groups and produce an inorganic arsenic-containing compound. For example, when tris(dimethylamino)arsine (TDMA) is bonded to silanol groups at the surface of the substrate, trace amounts of water may react with the dimethylamine groups of TDMA to remove these organic functional groups. In an illustrative embodiment, arsenic atoms diffusing into the body of the substrate may displace silicon atoms, germanium atoms, or both, within the lattice structure of the body of the substrate.

In particular embodiments, the arsenic atoms may diffuse to a particular depth with respect to the surface of the substrate. In one example, the arsenic atoms may diffuse into the body of the substrate such that the peak concentration of the dopant is achieved at a depth of no greater than about 20 nm from the surface of the substrate, no greater than about 10 nm from the surface of the substrate, no greater than about 7 nm from the surface of the substrate, or no greater than about 4 nm from the surface of the substrate. Additionally, the distribution of dopant in the substrate may be such that substantially no dopant in the silicon is present at a distance of 20 nm from a location of the peak dopant concentration in the substrate, at a distance of 10 nm from a location of a peak dopant concentration in the substrate, at a distance of 7 nm from a location of the peak dopant concentration in the substrate, or at a distance of 5 nm from the a location of the peak dopant concentration in the substrate. In an illustrative embodiment, the arsenic atoms may diffuse into the body of the substrate such that a location of the peak concentration of arsenic is achieved at a depth within a range of about 0.5 nm to about 9 nm and substantially no arsenic is present at a depth of about 3 nm to about 10 nm from a location of the peak arsenic concentration. In another illustrative embodiment, the arsenic atoms may diffuse into the body of the substrate to a depth within a range of about 1 nm to about 5 nm.

In an embodiment, adding the dopant to the body of the substrate may include an anneal process. In some cases, the anneal process may be conducted in an inert gas, such as nitrogen or argon, environment. In one embodiment, the anneal process may have a duration of at least 10 milliseconds, at least 0.5 seconds, at least 4 seconds, at least 20 seconds, at least 30 seconds, or at least 45 seconds. In another embodiment, the anneal process may have a duration of no greater than 135 seconds, no greater than 100 seconds, no greater than 75 seconds, or no greater than 50 seconds. In an illustrative embodiment, the anneal process can have a duration within a range of about 10 seconds to about 90 seconds, within a range of about 25 seconds to about 75 seconds, or within a range of about 30 seconds to about 60 seconds. In another illustrative embodiment, the anneal process may have a duration within a range of about 10 milliseconds to about 700 milliseconds.

In an additional embodiment, the anneal process may be conducted at a temperature of at least 600° C., at least 750° C., at least 900° C., or at least 1000° C. In a further embodiment, the anneal process may be conducted at a temperature of no greater than about 1200° C., no greater than about 1125° C., or no greater than about 1050° C. In an illustrative embodiment, the anneal process may be conducted at a temperature within a range of about 800° C. to about 1150° C. or within a range of about 900° C. to about 1050° C.

In some cases, prior to the annealing operation, a capping layer may be applied to the surface of the substrate. The capping layer may overlie the arsenic-containing compounds bonded to atoms of the substrate. In one embodiment, the capping layer may include $SiO_2$. In another embodiment, the capping layer can include silicon oxide formed using a plasma enhanced tetraethyl-orthosilicate process. In another embodiment, the capping layer can include silicon oxide formed with a liquid spin-on dielectric material. In some cases, the capping layer may have a thickness of at least 10 nm, at least 25 nm, or at least 40 nm. In other situations, the capping layer may have a thickness no greater than about 100 nm, no greater than about 80 nm, or no greater than about 60 nm. In an illustrative embodiment, the capping layer may have a thickness within a range of about 15 nm to about 55 nm or within a range of about 25 nm to about 45 nm. In a particular embodiment, after annealing of the substrate, the capping layer may be removed. For example, the capping layer may be removed by contacting the capping layer with a solution of dilute hydrofluoric acid.

Although the process 100 includes operations described with respect to blocks 102-108, in some cases, the process 100 can include additional operations. To illustrate, once the dopant has been added to the substrate, one or more additional operations can be performed to form a semiconductor device that includes ultra-shallow junctions formed from the doped substrate. In another illustration, the substrate may be contacted with a material that blocks some silicon atoms at the surface of the substrate from forming a bond with the arsenic-containing compound. In a particular situation, the blocking compounds may include reactive moieties that are analogous to those found on the arsenic-containing compound, but the blocking compounds do not include a dopant atom or atoms themselves.

In other cases, the process 100 may include fewer operations. For example, in an embodiment, the operations described with respect to 104 may be removed from the process 100 and the substrate can be contacted with the dopant solution without first modifying the surface of the substrate. Additionally, it should be noted that portions of the surfaces of the substrates described with respect to the process 100 may include exposed atoms of the substrate, such as exposed silicon atoms and/or exposed germanium atoms, while other portions of the surfaces of the substrate may be covered with particular materials, such as photoresist. Further, the order in which the operations of the process 100 are described is not intended to be construed as a limitation, and any number of the described operations can be combined in any order and/or in parallel to implement the process 100. In still further embodiments, although in some situations, the dopant solution may be described as including a solvent, in other cases, the dopant solution may not include a solvent.

Figure 2:
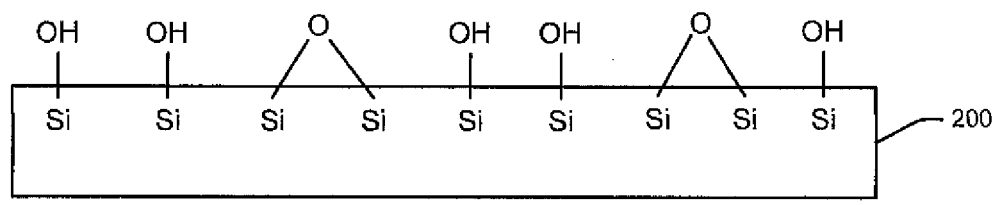
FIG. 2 illustrates an embodiment of a substrate having silicon atoms at a surface that can undergo one or more embodiments of processes described herein.

FIG. 2 illustrates an embodiment of a substrate 200 having silicon atoms at a surface that can undergo one or more embodiments of processes described herein. In a particular embodiment, the silicon atoms at the surface of the substrate 200 may not yet have been subjected to any processes to modify the surface of the substrate 200 as described herein. In an illustrative embodiment, the substrate 200 may illustrate the terminal bonding of silicon atoms at the surface of the substrate 200 when exposed to an air environment. Although not illustrated in FIG. 2, the silicon atoms at the surface of the substrate 200 may be bonded to each other, to other atoms of the substrate, or a combination thereof.

Figure 3:
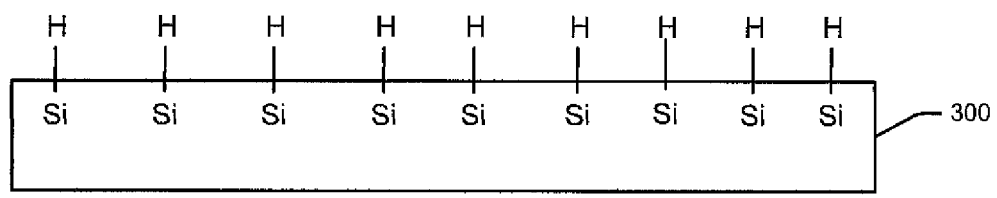
FIG. 3 illustrates an embodiment of a substrate having silicon atoms at a surface that have been subjected to one or more embodiments of processes described herein.

FIG. 3 illustrates an embodiment of a substrate 300 having silicon atoms at a surface that have been subjected to one or more embodiments of processes described herein. In one embodiment, the substrate 300 may illustrate the terminal bonding of silicon atoms at the surface of the substrate after being subjected to a surface modification process, such as a hydrogen termination process or a silanol formation process, as described herein.

Figure 4:
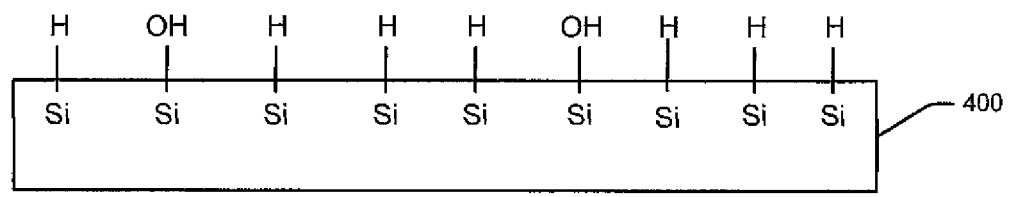
FIG. 4 illustrates an additional embodiment of a substrate having silicon atoms at a surface that have been subjected to one or more embodiments of processes described herein.

FIG. 4 illustrates an additional embodiment of a substrate 400 having silicon atoms at a surface that have been subjected to one or more embodiments of processes described herein. In the illustrative embodiment of FIG. 4, a portion of the silicon atoms at the surface of the substrate 400 are bonded to hydrogen atoms, while a number of other atoms at the surface of the substrate 400 are not hydrogenated. In one embodiment, the partial hydrogenation of the atoms at the surface of the substrate 400 may be due to the exposure of the hydrogenated substrate 300 of FIG. 3 to an air environment. In another embodiment, the partial hydrogenation of the atoms at the surface of the substrate 400 may be due to the incomplete reaction of atoms at the surface of the substrate 400 during a hydrogen termination process. In another embodiment, the partial hydrogenation may be a result of exposing a hydrogen terminated surface to an oxidizing liquid. In yet another embodiment, the partial hydrogenation may be a result of the presence of dissolved oxygen in the hydrogen termination solution. In a further embodiment, the partial hydrogenation may be a result of exposing the hydrogen terminated surface to deionized water that contains dissolved oxygen. Combinations of any or all of the above steps are also possible to form partial hydrogenation.

Figure 5:
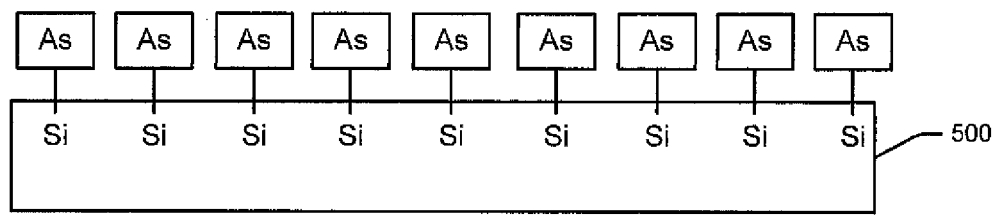
FIG. 5 illustrates an embodiment of a substrate having silicon atoms at a surface bonded to an arsenic-containing compound.

FIG. 5 illustrates an embodiment of a substrate 500 having silicon atoms at a surface bonded to an arsenic-containing compound (illustrated as "As" in FIG. 5). In one embodiment, the silicon atoms at the surface of the substrate may be bonded directly to an As atom of the arsenic-containing compound. In another embodiment, the silicon atoms at the surface of the substrate may be bonded to atoms of the arsenic-containing compound other than the As atom or atoms of the arsenic-containing compound. In a particular embodiment, the substrate 500 may have been contacted with one or more of the dopant solutions described herein, such as via the processes described with respect to operation 106 of FIG. 1.

Figure 6:
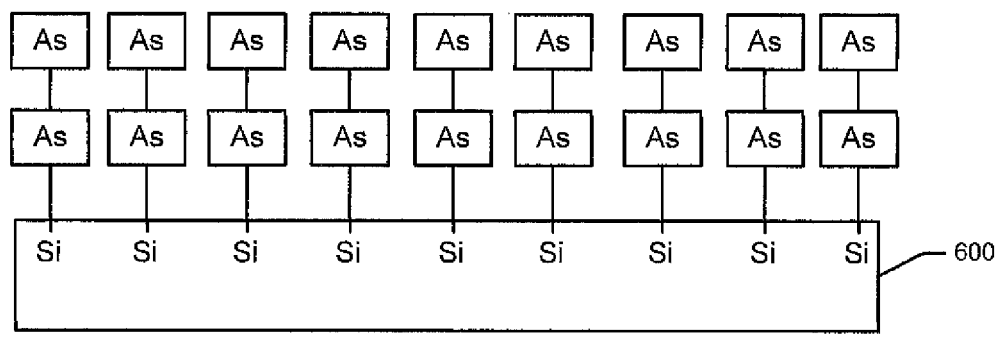
FIG. 6 illustrates an embodiment of a substrate having silicon atoms at a surface bonded to multiple layers of an arsenic-containing compound.

FIG. 6 illustrates an embodiment of a substrate 600 having silicon atoms at a surface bonded to multiple layers of an arsenic-containing compound (illustrated as "As" in FIG. 6). In a particular embodiment, the substrate 600 may represent the substrate 500 of FIG. 5 after being subjected to an additional process of contacting the substrate 500 with one or more of the dopant solutions described herein.

Figure 7:
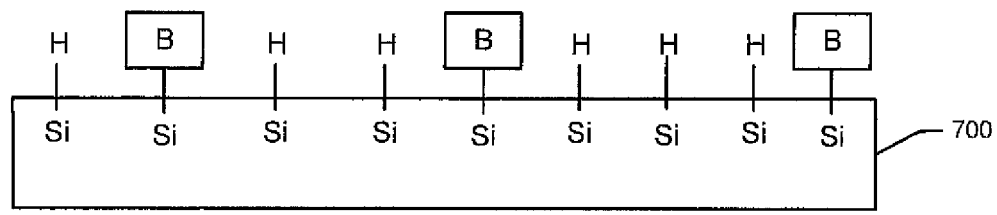
FIG. 7 illustrates an embodiment of a substrate having silicon atoms at a surface bonded to a blocking molecule.

FIG. 7 illustrates an embodiment of a substrate 700 having silicon atoms at a surface bonded to a blocking molecule (illustrated as "B" in FIG. 7). In some cases, to control the concentration of the dopant in the substrate 700, a substrate, such as the substrate 200 of FIG. 2, the substrate 300 of FIG. 3, or the substrate 400 of FIG. 4, can be subjected to one or more processes to bond blocking molecules with a portion of the silicon atoms at the surface of the substrate. In an embodiment, the blocking molecules may not form a bond with one or more of the arsenic-containing compounds described herein under the process conditions described herein. In a particular embodiment, the blocking compounds may include reactive moieties that are analogous to those found on the arsenic-containing compound, but do not include a dopant atom or atoms themselves. Some examples of blocking molecules include alpha olefins, terminal alkynes, carboxylic esters, acyl halides, isocyanates, or combinations thereof.

Figure 8:
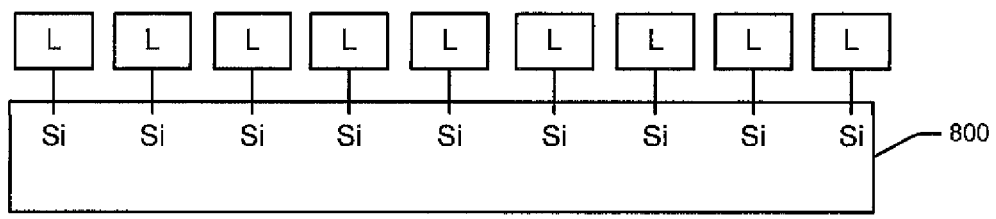
FIG. 8 illustrates an embodiment of a substrate having silicon atoms at a surface bonded to a linking moiety.

FIG. 8 illustrates an embodiment of a substrate 800 having silicon atoms at a surface bonded to a linking moiety (illustrated as "L" in FIG. 8). In one embodiment, the linking moiety may be bonded to silicon atoms at the surface of a substrate, such as the substrate 200 of FIG. 2, the substrate 300 of FIG. 3, or the substrate 400 of FIG. 4, by subjecting the substrate to one or more of the processes described with respect to operation 104 in FIG. 1 to treat the surface of the substrate to produce a modified surface of the substrate.

Figure 9:
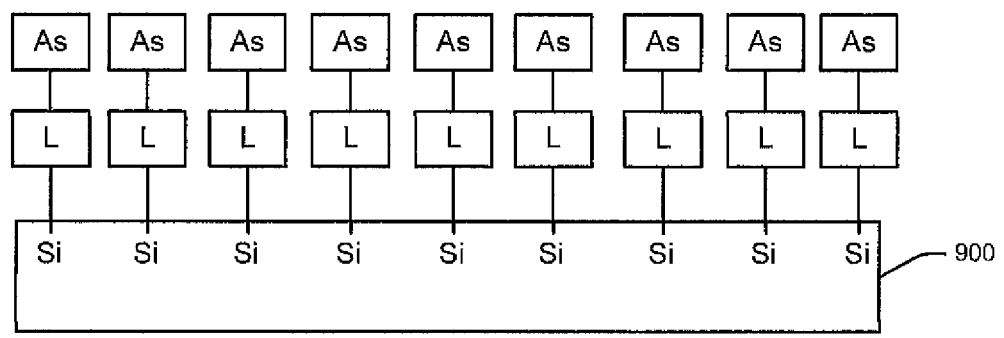
FIG. 9 illustrates an embodiment of a substrate having silicon atoms at a surface bonded to a linking moiety with an arsenic-containing compound bonded to the linking moiety.

FIG. 9 illustrates an embodiment of a substrate 900 having silicon atoms at a surface bonded to a linking moiety (illustrated as "L" in FIG. 9) and an arsenic-containing compound (illustrated as "As" in FIG. 9) is bonded to the linking moiety. In one embodiment, the arsenic-containing compound may be bonded to the linking moiety by one of the processes described herein with respect to operation 106 of FIG. 1.

Substrates formed according to embodiments herein may have certain advantages over the state of the art. In particular, substrates formed according to embodiments described herein may have a more uniform distribution of dopant atoms than the distribution provided by conventional processes, such as ion implantation. Additionally, the concentration of the dopant in the substrate can be controlled by using blocking molecules or by using multiple layers of arsenic-containing compounds bonded to atoms of the surface of the substrate. Furthermore, the depth of the diffusion of the dopant atoms can be controlled such that semiconductor devices with ultra-shallow junctions less than 14 nm can be formed. In some cases, the ultra-shallow junctions may be formed due to the decreased damage to the substrate prior to the annealing process, which may limit transient enhanced diffusion that is often present when conventional doping techniques, such as ion implantation or knock-in processes are utilized.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

The concepts described herein will be further described in the following examples, which do not limit the scope of the disclosure described in the claims.

EXAMPLES

Example 1

A composition of matter having the chemical formula:

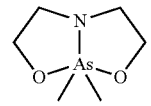

is formed when about 3.047 g (22 mmol) of cacodylic acid and about 2.32 g (22 mmol) of diethanolamine are suspended in about 60 mL of toluene and heated to reflux with azeotropic removal of water using a Dean-Stark apparatus under an atmosphere of nitrogen for about 16 hours. After cooling to about 18-25° C., the toluene is removed in vacuo to produce a substance including the composition of matter. The substance appears as a red oil and 1H NMR analysis shows the substance to have residual impurities, such as toluene and diethanolamine.

Example 2

A composition of matter having the chemical formula:

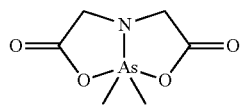

is formed when about 2.875 g of cacodylic acid and about 2.77 g of iminodiacetic acid are suspended in 60 mL of toluene in a 100 mL round-bottomed flask fitted with a 10 mL Dean-Stark trap, a nitrogen bubbler and a magnetic stirrer. The mixture is heated at reflux for about 18 hours via oil bath with azeotropic removal of about 0.7 mL—about 0.8 mL of water. After cooling to room temperature, the toluene is removed in vacuo to form a substance that appears as a colorless crystalline solid. 1HNMR (dmso d6) analysis indicates that the composition of matter is formed in near-quantitative yield with 4.916 g being isolated.

Example 3

A composition of matter having the chemical formula:

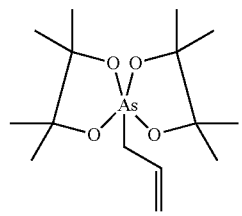

is formed when about 1.741 g of allylarsonic acid and about 2.479 g of pinacol are suspended in about 60 mL of toluene and heated at reflux with azeotropic removal of water overnight. Gravity filtration of a small amount of suspension and removal of the toluene in vacuo from the filtrate produce about 3.6 g of a substance that appears as a colorless oil.

Example 4

A composition of matter having the chemical formula:

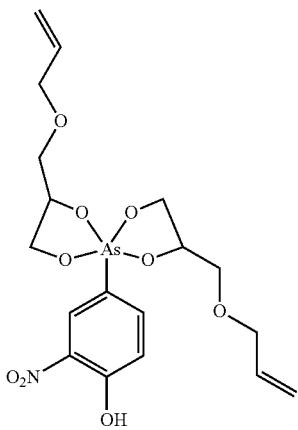

is formed when about 6.1 g of (4-hydroxy-3-nitrophenyl) arsonic acid and about 6.13 g of 3-(alloxy)propane-1,2-diol are suspended in about 60 mL of toluene and heated to reflux with the azeotropic removal of water for about 16 hours. After cooling, the toluene is removed in vacuo to give about 11 g of a substance that includes the composition of matter. The substance appears as a yellow oil.

Example 5

A composition of matter having the chemical formula:

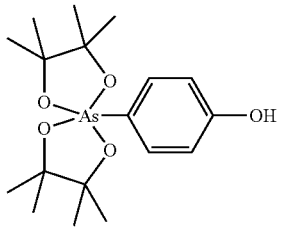

is formed when about 4.36 g of 4-hydroxyphenylarsonic acid and about 4.73 g of pinacol are refluxed together in about 80 mL of toluene for about 16 hours with removal of the water using a Dean-Stark trap. The toluene is removed in vacuo to produce about 7.47 g of a pale yellow crystalline solid.

Example 6

A composition of matter having the chemical formula:

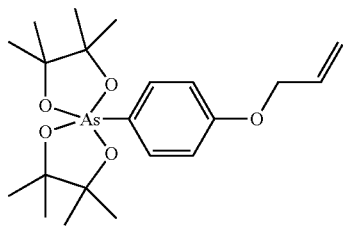

is formed when about 0.52 g of the bis-pinacol adduct of phenol-4-arsonic acid from Example 5 is treated with about 0.39 g of potassium carbonate and about 1 mL of allyl bromide in about 5 mL of dimethylformamide and swirled briefly. The mixture is allowed to stand at about 18° C. to about 25° C. for about a week. About 3-5 mLs of glacial acetic acid are then added to the mixture with a few drops of 33% HBr in HOAc. Water is added to precipitate the product as colorless needles. The needles are filtered and washed with a little aqueous ethanol. The yield is about 0.40 g after drying in air on the suction filter for about 16 hours.

Example 7

A composition of matter having the chemical formula:

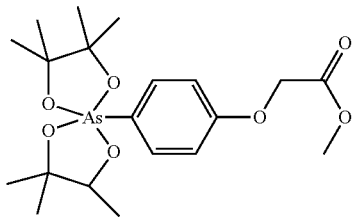

is formed when about 2.70 g (6.74 mmol) of the bis-pinacol adduct of phenol-4-arsonic acid of Example 5, about 1.66 g (12.01 mmol) of potassium carbonate, and about 0.725 mL (7.66 mmol) of methyl bromoacetate are stirred by magnetic stirrer together in about 10.5 mL of anhydrous dimethylformamide overnight. The heterogeneous mixture is diluted with about 20 mL of glacial acetic acid and treated with a few drops of 33% HBr in HOAc. About 80 mL of water is added and the mixture is stirred briefly. The resulting colorless precipitate is removed by vacuum filtration, and washed with a water/ethanol mixture to yield 1.95 g of a substance including the composition of matter after drying.

Example 8

A composition of matter having the chemical formula:

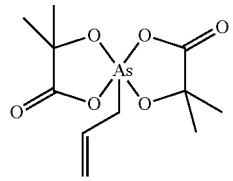

is formed when about 3.32 g of allyarsonic acid and about 4.16 g of hydroxyisobutyric acid are refluxed under $N^2$ overnight in about 60 mL of toluene with azeotropic removal of water using a Dean/Stark trap. After removal of solvent, the product is isolated as about 5.55 g of colorless crystals. Another 250 mg is recovered after re-dissolving a remainder from the original flask and evaporation in a smaller vessel.

Example 9

A composition of matter having the chemical formula:

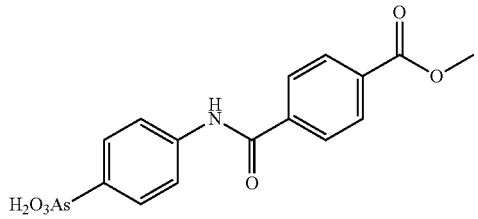

is formed when about 4.05 g (18.66 mmol) of p-arsinilic acid is slurried in about 40 mL of absolute ethanol and about 4.45 g (22.41 mmol) of solid methyl terephthaloyl chloride is added to the mixture. The mixture is stirred at room temperature, with perhaps a very, very mild exothermic reaction upon addition/dissolution of the acid chloride. Upon complete dissolution in about 5 min, about 1-3 mL of water is added dropwise and the product precipitates as a colorless powder. The precipitate is removed by suction filtration and dried on the filter for about 16 hours to yield about 3.96 g of the product. Two more crops of about 0.9 g and about 1.1 g of the product are recovered. A 1HNMR analysis indicates that the additional crops have a small amount of contamination of p-arsinilic acid.

Example 10

A composition of matter having the chemical formula:

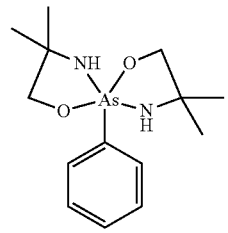

is formed when about 3 g of phenylarsonic acid and about 2.79 g of 2-amino-2-methylpropan-1-ol are suspended in about 60 mL of toluene and heated to reflux with the azeotropic removal of water for about 16 hours. After cooling, the toluene is removed in vacuo to produce about 4.83 g of the desired adduct as a colorless, but slightly sticky, crystalline solid. The solid is re-slurried in about 60 mL of hexanes at room temperature, and then subject to suction filtration on a coarse frit by washing three times on the filter with about 20 mL of hexanes for each wash. After drying, the desired compound is isolated as about 4.03 g of colorless crystals.

Example 11

A composition of matter having the chemical formula:

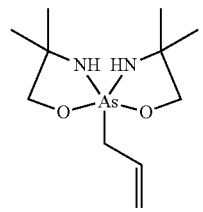

is formed when about 1.707 g of allylarsonic acid and about 1.93 g of 2-amino-2-methyl-1-propanol are suspended in about 60 mL of toluene and heated at reflux under nitrogen with azeotropic removal of water for about 16 hours. After cooling, the toluene is removed in vacuo to produce about 3 g of a semi-solid off-white residue. The residue is boiled briefly in about 60 mL of hexanes, and, after cooling to about 18-25° C., near-colorless needles are formed, collected by suction filtration and washed with hexanes to yield about 1.15 g of the product.

Example 12

A composition of matter having the chemical formula:

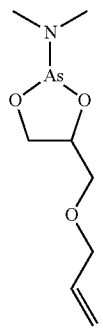

is formed when at room temperature, about 0.5 g (0.445 mL, 2.414 mmol, 1.1 equivalents) of tris(dimethylamino)arsine (TDMA), is added to about 10 mL dry hexane in a 25 mL round-bottom flask, and then about 0.29 g (0.27 mL, 2.19 mmol, 1.0 equivalents) of 3-(allyloxy)propane-1,2-diol is added dropwise into the system. The mixture is heated to reflux under nitrogen for about one hour, and then cooled to room temperature. Removal of the solvent in vacuum gives crude 4-((allyloxy)methyl)-N,N-dimethyl-1,3,2-dioxarsolan-2-amine as an oil.

Example 13

A composition of matter having the chemical formula:

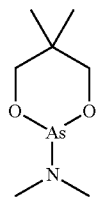

is formed when about 0.47 g (4.5 mmol, 1.0 equivalents) of 2,2-dimethylpropane-1,3-diol is added to about 15 mL hexane, and then about 1.04 g (0.92 mL, 5.0 mmol, 1.1 equivalents) of tris(dimethylamino)arsine (TDMA) is added dropwise to the flask. The mixture is heated to reflux under nitrogen for about 1.5 hours, and then cooled to room temperature. Removal of the solvent in vacuum gives crude N,N,5,5-tetramethyl-1,3,2-dioxarsinan-2-amine as an oil.

What is claimed is:

1. A process, comprising:
   preparing a solution including a dopant and a solvent, the dopant including arsenic; and
   contacting a substrate with the solution, wherein the solution has a flashpoint that is at least approximately equal to or greater than a minimum temperature capable of causing attachment between at least a portion of atoms of the substrate and an arsenic-containing compound of the solution in a duration of no greater than 2.5 hours.

2. The process of claim 1, further comprising treating a surface of the substrate to produce a modified surface of the substrate.

3. The process of claim 2, wherein the modified surface of the substrate includes at least a portion of a plurality of silicon atoms at the surface being bonded to hydrogen atoms.

4. The process of claim 2, wherein the modified surface of the substrate includes at least a portion of a plurality of silicon atoms at the surface being bonded to a respective linking moiety.

5. The process of claim 1, wherein the arsenic-containing compound includes an organoarsenic compound, and contacting the substrate with the solution includes covalently bonding the organoarsenic compound to at least a portion of a plurality of silicon atoms at a surface of the substrate.

6. The process of claim 4, wherein the arsenic-containing compound includes an organoarsenic compound, and contacting the substrate with the solution includes covalently bonding the organoarsenic compound to at least a portion of the respective linking moieties.

7. The process of claim 1, further comprising adding the dopant to the substrate.

8. The process of claim 7, wherein adding the dopant to the substrate includes annealing the substrate.

9. The process of claim 1, wherein the substrate includes silicon, germanium, or a combination thereof.

10. A solution comprising:
    a solvent; and
    an arsenic-containing compound;
    wherein the solution has a flashpoint that is at least approximately equal to a minimum temperature capable of initiating a reaction between the solution and silicon within a duration of no greater than 2.5 hours.

11. The solution of claim 10, wherein the solvent includes 4-hydroxy butanoic acid, a glycol ether (e.g., di-ethylene glycol di-butyl ether, tetra-ethylene glycol di-methyl ether (tetraglyme)), 4-formylmorpholine, phenylacetic acid, a C9 alcohol, a C10 alcohol, 3-nonanone, phenylpropyl ether, dimethylsulfoxide (DMSO), cyclooctanone, furfuryl acetone, isophorone, di-hexyl ether, 2-nonanone, phenyl propyl ether, hexyl benzene, mesitylene, N-methylpyrrolidone (NMP), an alkanolamine, acetonitrile, toluene, dioxane, tetrahydrofuran (THF), or combinations thereof.

12. The solution of claim 10, wherein the flashpoint of the solution is within a range of about 50° C. to about 115° C.

13. The solution of claim 10, wherein the solution includes the arsenic-containing compound within a range of about 2 wt % to about 11 wt % of the total weight of the solution.

14. A substrate comprising:
    a surface having a plurality of silicon atoms; and
    an arsenic-containing compound covalently bonded to at least a portion of the plurality of the silicon atoms.

15. The substrate of claim 14, wherein the substrate includes a plurality of layers of one or more arsenic-containing compounds covalently bonded to the at least a portion of the plurality of silicon atoms.

16. A composition of matter comprising:

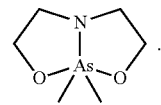

17. A composition of matter comprising:

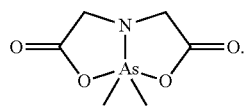

18. A composition of matter comprising:

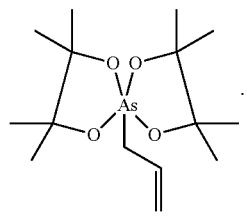

19. A composition of matter comprising:

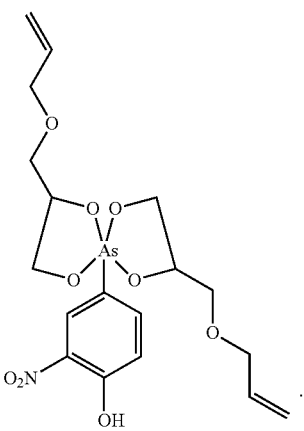

20. A composition of matter comprising:

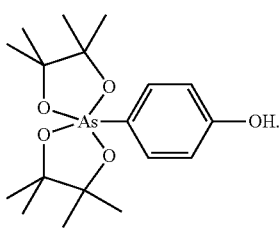

21. A composition of matter comprising:

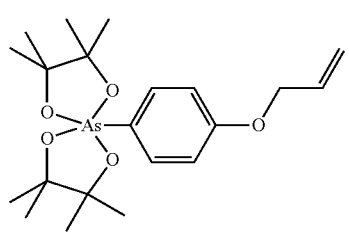

22. A composition of matter comprising:

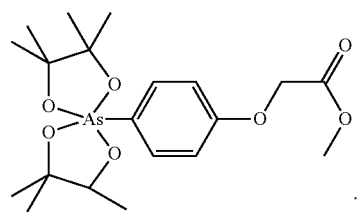

23. A composition of matter comprising:

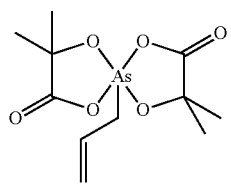

24. A composition of matter comprising:

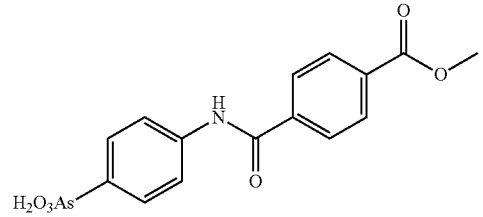

25. A composition of matter comprising:

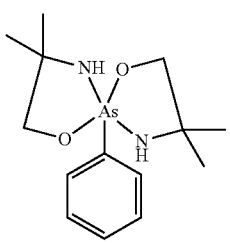

26. A composition of matter comprising:

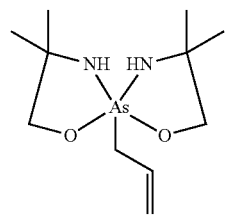

27. A composition of matter comprising:

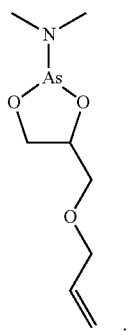

28. A composition of matter comprising:

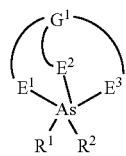

wherein, $R^1$ and $R^2$ each, independently, include a hydrocarbyl group, a substituted hydrocarbyl group, or a silyl group; $R^1$ and $R^2$ collectively form a bridging group; $E^1$, $E^2$, and $E^3$, each, independently, include N, O, or S atoms; G1 includes a group linking $E^1$, $E^2$, and $E^3$; and $G^1$ includes a hydrocarbyl group, a substituted hydrocarbyl group, or a silyl group.

29. The composition of matter of claim 28, wherein $E^1$, $E^2$, $E^3$, or a combination thereof, includes N, and N is further substituted by hydrogen, a hydrocarbyl group, a substituted hydrocarbyl group, or a silyl group.

30. A composition of matter comprising:

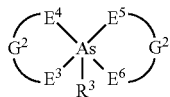

wherein $R^3$ includes a hydrocarbyl group, a substituted hydrocarbyl group, or a silyl group; $E^4$, $E^5$, $E^6$, and $E^7$ each, independently, include O, S, or N; $G^2$ and $G^3$ are residues of moieties that comprise $E^4$ and $E^5$, and $E^6$ and $E^7$, respectively; $G^2$ and $G^3$ include a hydrocarbyl group, a substituted hydrocarbyl group, or a silyl group; wherein the moiety or moieties borne by at least one of $R^3$, $G^2$, and $G^3$ is selected from a group consisting of: a terminally unsaturated hydrocarbyl group; a carboxylate ester group, an activated ester group, an arsonic acid; an alkene conjugated to at least one ketone, an alkene conjugated to at least one aldehyde group, a an alkene conjugated to at least one cyano group, an alkene conjugated to at least one nitro group, an alkene conjugated to at least one sulfonyl group, an alkene conjugated to at least one carboxylic ester group, an alkene conjugated to at least one activated ester group, and an alkene conjugated to at least one arsonic acid group.

31. The composition of matter of claim 30, wherein the $E^4$, $E^5$, $E^6$, $E^7$, or a combination thereof, include N, and N is further substituted by hydrogen, a hydrocarbyl group, a substituted hydrocarbyl group, or a silyl group.

32. A composition of matter comprising:

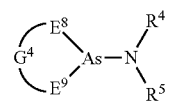

wherein $R^4$ and $R^5$ each, independently, include hydrogen, a hydrocarbyl group, a substituted hydrocarbyl group, or a silyl group, wherein $E^8$ and $E^9$ each, independently, represent O, S, or N, wherein $G^4$ is a group linking $E^8$ and $E^9$ and, $G^4$ includes a hydrocarbyl group, a substituted hydrocarbyl group, a silyl group, an alkenyl group, or an alkynyl group, and wherein one or more moieties borne by at least one of $R^4$, $R^5$, and $G^4$ is selected from a group consisting of: a terminally unsaturated hydrocarbyl group; a carboxylate ester group, an activated ester group, an arsonic acid; an alkene conjugated to at least one ketone, an alkene conjugated to at least one aldehyde group, a an alkene conjugated to at least one cyano group, an alkene conjugated to at least one nitro group, an alkene conjugated to at least one sulfonyl group, an alkene conjugated to at least one carboxylic ester group, an alkene conjugated to at least one activated ester group, and an alkene conjugated to at least one arsonic acid group.

33. The composition of matter of claim 32, wherein $E^8$, $E^9$, or a combination thereof, includes N, and N is further substituted by hydrogen, a hydrocarbyl group, a substituted hydrocarbyl group, or a silyl group.

34. The process of claim 1, wherein the arsenic-containing compound includes at least one of the compositions of matter of claims 16-33.

* * * * *